Oct. 20, 1936. J. E. BJURSTROM Re. 20,135

HOT AIR RESPIRATOR

Original Filed March 21, 1932

INVENTOR.
JOHN E. BJURSTROM

BY Andrew E. Carlson

ATTORNEY.

Reissued Oct. 20, 1936

Re. 20,135

UNITED STATES PATENT OFFICE 20,135

HOT AIR RESPIRATOR

John E. Bjurstrom, St. Paul, Minn.

Original No. 1,982,412, dated November 27, 1934, Serial No. 600,172, March 21, 1932. Application for reissue March 2, 1936, Serial No. 66,777

8 Claims. (Cl. 128—212)

This invention relates to apparatus for the thermo-therapeutic treatment of infected cavities, membranes, and tissues of the head, and particularly those of or which communicate with the mouth, throat, nasal and other respiratory passages; and the main object is to provide a simple, efficient, and effective hot air respirator which when used by the patient will not only merely alleviate his discomfort but will when properly employed, relieve the pathological condition causing the illness and pain.

It is generally acknowledged that diseases such as laryngitis, sinusitis, rhinitis, bronchitis, and common head colds, chronic or otherwise, are caused by infected areas or tissues which, when inflamed and irritated, impede and obstruct normal drainage of sinuses and other cavities, and when this occurs the situation is aggravated and normal healing is accordingly retarded and often prevented.

It is equally well known that infected tissue, in any part of the body, will almost invariably respond to artificial thermogenic application or treatment, providing heat can be applied at sufficiently high temperatures and over sufficiently lengthy and frequent periods of time. The generally accepted theory for this physiological response is that the increased temperature drives off or kills the invading germ life, and also thins out the blood and lymphatic fluids so that they may more readily penetrate into and circulate through congested and infected areas to carry off poisons and inactive tissue material and in turn resupply healthy body building cells. The healing effect of thermo-therapeutic treatment is particularly evidenced and recognized where the infected, diseased, or damaged tissue is exposed sufficiently so that heat by water or other mediums can be conveniently applied.

The primary difficulty in the thermogenic treatment of the respiratory tract and areas is that of suitably applying the heat without interfering with the patient's breathing or comfort, it being understood that heat can only be applied to these membranes within a limited range of temperature and must therefore be continued over substantial periods of time to be effective. If the patient is placed in a room wherein the air is heated sufficiently so that it will have the desired curative effect on the respiratory surfaces when inhaled by the patient, then it will obviously be so hot on his body surfaces as to render the treatment exceedingly uncomfortable, and might in fact give rise to other and more serious reactions. Hence such method is entirely impractical.

The local application of hot air supplied for inhaling purposes through a tube from a remote source, such as suggested in the patent to Morris, No. 792,230, issued June 13th, 1905, is also found to be entirely impractical as it either requires constant manipulation of the application nozzle by the patient, or if held to the nose or mouth would prevent exhaling and otherwise seriously interfere with the patient's comfort. Such a device would obviously be useless for producing hot air for inhalation purposes over long periods of time and particularly when the patient is sleeping.

To overcome the aforementioned difficulties and objections, I have designed a respirator which will provide hot air for inhalation purposes, under proper control, and without, to any appreciable extent, interfering with the patient's comfort or normal respiration. This respirator comprises a mask, adapted to be fitted over the mouth and nose and attached by means passing around the head, and an electric heating element, exhaling valve and a current control unit all carried by the mask and coordinated therewith in such a manner that the heating element will be disposed in the passageway for air passing into and through the mask under the inhalation action, and may be adjusted as to temperature by the control unit, while the valve permits exhalation with no appreciable resistance and in a direction other than through the heating element or its chamber.

In the accompanying drawing, which illustrates a preferred embodiment of the invention—

Figure 2:
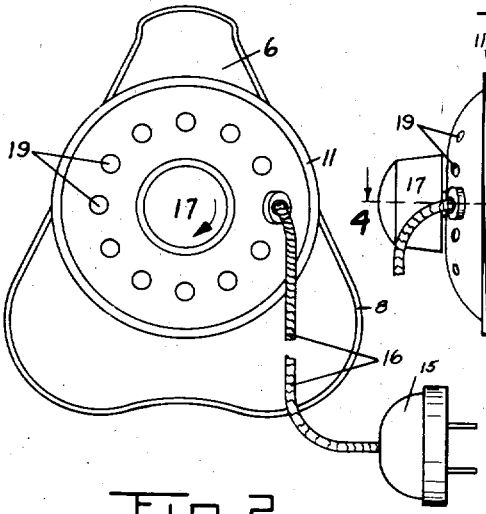
Fig. 2 is a front elevation of the device as shown in Fig. 1.
Figure 3:
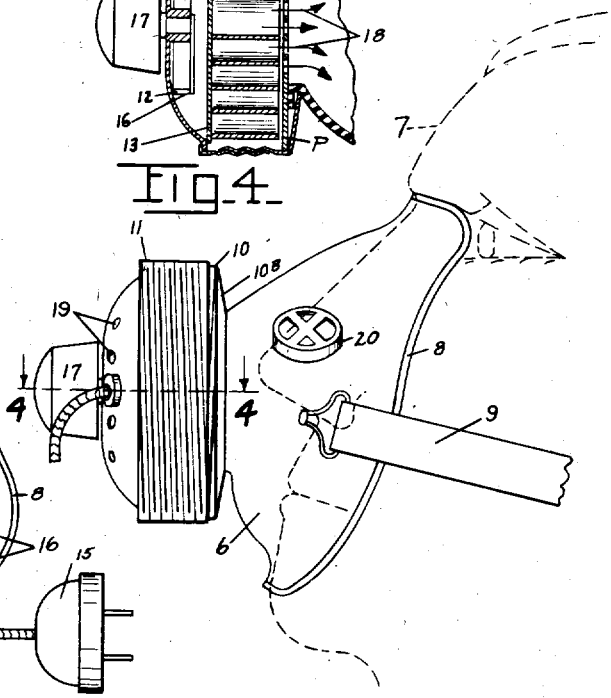
Fig. 3 is a side elevation of the respirator, indicating by dotted lines how it is applied to the face over the mouth and nose.

Referring to the drawing more particularly and by reference characters, 6 designates a facial mask, made of rubber or other suitable semi-flexible material and is so formed as to cover the nose and mouth of the patient (indicated by dotted lines 7) as shown in Fig. 3. The face contact part of the mask proper preferably extends from the chin to the bridge of the nose vertically, and is about four inches wide at its base with a tapering contour toward the upper end, as generally indicated in Fig. 2.

The rim of the mask and adjacent inner areas may be suitably padded as at 8, and the mask being flexible, its rim parts can be pressed in air tight condition against the face and may be held in place by a suitable elastic band 9 adapted to be placed around the head. The mask extends forwardly of the nose, and is tapered in that direction to a preferably circular and exteriorally flanged opening, the flange of which is designated 6F in Fig. 4, said opening being approximately in a vertical plane when the mask is in position on the face, as indicated in Fig. 3.

To the forward mask flange 6F is fixed an electric heating unit comprising a two part metal shell, of which one section 10 has an axial opening in its wall 10B, for receiving the mask flange 6F; and this member section 10 has an annular flange portion which is threaded to receive a correspondingly threaded front member or shell 11. The front wall of the member 11 is provided with a rheostat 12 having circuitous connection with an electric resistance coil 14 mounted on a plate 13, which plate is of a size to be removably retained concentrically in the forward end of the chamber defining the heating unit. The plate 13 is provided with an aperture 13G (see Fig. 4) through which the circuit wires may extend, and this aperture 13G also provides passageway for the air to be heated.

Figure 4:
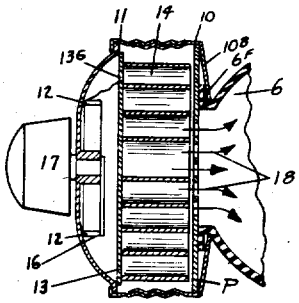
Fig. 4 is a diametrical cross sectional detail view through the heating element and enclosure, on line 4—4 in Fig. 3.

The heating member 14 may be formed in various manners, but is here shown as comprising a resistance coil formed of flat material, and secured upon the plate 13 in spiral formation, as indicated in Fig. 4. Electric current is conducted from any suitable source through a plug 15 and cord 16 to the rheostat 12, which rheostat regulates the amount of current to be conducted to the resistance coil 14, the rheostat being controlled by a turnable button 17 projecting axially in front of the heating device.

Figure 1:
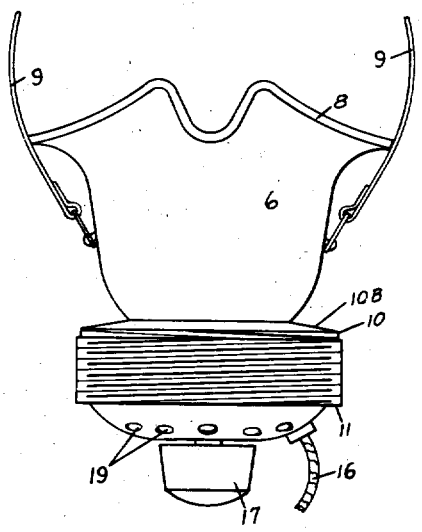
Fig. 1 is a top or plan view of the respirator.
Figure 5:
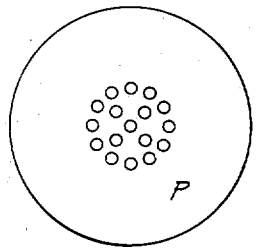
Fig. 5 is a detail elevation of a perforated plate member P, employed adjacent to the heating unit and through which air is drawn into the mask after first being heated by the heating unit.

As shown in Figs. 1, 2, and 3, the front wall of the heater casing is provided with perforations 19 for the inward passage of air. It will be understood that the air movement inwardly through the heating unit and to the patient's mouth or nose is caused entirely by the inhaling or normal respiratory action of the person wearing the device; and that the parts are so arranged that they will offer no appreciable or noticeable resistance to the normal breathing action. When the breath is drawn in, air is drawn through the holes 19 toward the plate 13, and then passes through the aperture 13G toward the outer periphery of the plate, and thence through the heating unit 14 and the holes in the plate P to the face. It will be noted that the aperture 13G is so arranged that the air drawn in through it will be forced to circulate inwardly through the spiral formation of the unit 14 before it can reach and escape through the perforations which are somewhat centrally grouped in the plate P; and consequently this air so circulated will be raised to the desired temperature.

When the patient exhales, the valve 20 comes into play, and as it operates with practically no resistance the air passes outwardly therethrough in preference to a return movement through the heating unit.

As an important consideration or feature of the present invention, it should be observed that the heating element 14 is insulated as far as possible from heating the mask proper, and is not intended to increase the temperature of either the mask or any of the parts of the apparatus; and is to that extent distinguishable from devices which have heating elements, the primary purpose of which is to vaporize a medicament.

In the present instance there is no conversion of liquid anaesthetics or other preparations into fumes or gaseous conditions, and it is the sole purpose of the heating element to heat only the air passing through the respirator and into the mouth or nose of the patient. To this end the heating element is so arranged that it will be disposed directly in the passageway of the inhaled air, and will in this manner most effectively heat the air flowing through the passageway without heating other parts of the device.

It will be understood that the accompanying drawing illustrates only a preferred embodiment of the invention, and that various modifications may be made without departing from the scope and spirit of the invention as set forth in the following claims. Having now therefore fully disclosed and described my invention, what I claim to be new and desire to protect by reissue Letters Patent is:

1. In a respirator of the class described and including a flexible mask adapted to bear against the face and inclose the respiratory organs; said mask provided with an opening directly forward of said organs, an air heating chamber secured to said opening part of the mask, electric heating means mounted within said chamber, said chamber provided in its forward part with air intake apertures, a perforated plate adjacent the mask opening and within the inner part of said chamber, said heating means comprising a resistance coil in an upright plane and in the path of air currents inhaled into the mask, said heating chamber comprising two separable cylindrical housing members, an upright non-conductive perforate plate retained concentrically in the forward part of the chamber and said resistance coil secured to the inner face of said plate, a rheostat in the chamber forward of said resistance coil and electric conductors connecting the rheostat and the coil, connecting means for supplying electric current to said coil through said rheostat, and a rheostat control button accessible exteriorly of the housing for the purpose set forth.

2. An apparatus for thermotherapeutic treatment of the respiratory tract comprising a mask for application over the nose and mouth, said mask having a passageway for the inhalation of air therethrough and into the mask, and an electric heating element secured to the mask so as to be supported and carried by the mask, said element being disposed in said passageway with its surfaces exposed to the air passing therethrough to heat such air.

3. An apparatus for thermotherapeutic treatment of the respiratory tract comprising a mask for application over the nose and mouth, said mask having a passageway for the inhalation of air therethrough and into the mask, and an electric heating element mounted on the mask so as to be supported and carried thereby and disposed in said passageway with its surfaces exposed to the air passing therethrough to heat such air, said heating element being arranged to circuitously lengthen the air travel through the passageway to thereby effectively increase the heat transmitting property of the element.

4. An apparatus for thermotherapeutic treatment of the respiratory tract comprising a mask for application over the nose and mouth, said mask having a passageway for the inhalation of air therethrough and into the mask, and a spirally formed heating element disposed in said passageway and with its surfaces exposed to the air passing therethrough to thereby heat the air.

5. An apparatus for thermotherapeutic treatment of the respiratory tract comprising a mask for application over the nose and mouth, said mask having a passageway for the inhalation of air therethrough and into the mask, a chamber unit attached to the mask over said passageway and having openings for the movement of air therethrough and into the mask, an electric heating element within said chamber and having surfaces exposed for direct contact with the air passing through the unit and about the element.

6. An apparatus for thermotherapeutic treatment of the respiratory tract comprising a mask for application over the nose and mouth, said mask having a passageway for the inhalation of air therethrough and into the mask, a chamber unit attached to the mask over said passageway and having openings for the movement of air therethrough and into the mask, an electric heating element within said chamber and having surfaces exposed for direct contact with the air passing through the unit and about the element, and a device for controlling the electric current to the heating element.

7. An apparatus for thermotherapeutic treatment of the respiratory tract comprising a mask for application over the nose and mouth, said mask having a passageway for the inhalation of air therethrough and into the mask, a chamber unit attached to the mask over said passageway and having openings for the movement of air therethrough and into the mask, an electric heating element within said chamber and having surfaces exposed for direct contact with the air passing through the unit and about the element, a heat control device mounted within the chamber unit, and an adjuster element for the heat control device disposed and operative from outside of the heat chamber.

8. An apparatus for thermotherapeutic treatment of the respiratory tract comprising a mask for application over the nose and mouth, said mask carrying a chamber having a passageway for the inhalation of air therethrough and into the mask, and an electric heating element disposed in said chamber with its surfaces exposed to the air passing therethrough to heat such air, said heating element being arranged to circuitously lengthen the air travel through the passageway to thereby effectively increase the heat transmitting property of the element, and means for releasably securing the mask, chamber and heating element upon the face.

JOHN E. BJURSTROM.